United States Patent [19]
Mark et al.

[11] Patent Number: 4,721,813
[45] Date of Patent: Jan. 26, 1988

[54] METHOD FOR THE OXIDATION OF MERCAPTOALKANOLS TO DITHIODIGLYCOLS

[75] Inventors: Harold W. Mark; John S. Roberts, both of Bartlesville, Okla.

[73] Assignee: Phillips Petroleum Company, Bartlesville, Okla.

[21] Appl. No.: 900,214

[22] Filed: Aug. 25, 1986

[51] Int. Cl.$^4$ ............................................ C07C 148/00
[52] U.S. Cl. ...................................................... 568/22
[58] Field of Search ...................... 568/22, 26, 21, 23, 568/24, 25

[56] References Cited

U.S. PATENT DOCUMENTS

| | | | |
|---|---|---|---|
| 3,039,855 | 6/1962 | Urban | 423/573 R |
| 3,392,201 | 7/1968 | Warner | 568/26 |
| 4,078,992 | 3/1978 | Douglas | 208/206 |
| 4,288,627 | 9/1981 | Kubicek | 568/26 |

Primary Examiner—Mary E. Ceperley
Attorney, Agent, or Firm—S. E. Reiter

[57] ABSTRACT

A method for the conversion of mercaptoalkanols to dithiodiglycols having good color properties and low residual odor is provided. Mercaptalkanols are reacted in the presence of small amounts of anhydrous ammonia and an oxygen-containing gas in the absence of any metal-containing catalysts to produce the desired dithiodiglycol products.

7 Claims, No Drawings

METHOD FOR THE OXIDATION OF MERCAPTOALKANOLS TO DITHIODIGLYCOLS

This invention relates to the oxidation of mercaptoalkanol compounds to produce disulfide compounds. In one aspect, the present invention relates to the ammonia catalyzed oxidation of mercaptan-containing compounds to disulfide compounds. In another aspect, the present invention relates to the production of relatively odor free, low color disulfide compounds.

BACKGROUND OF THE INVENTION

While the oxidation of mercaptans to disulfides can readily be carried out in the presence of a variety of catalysts, a problem frequently encountered is the formation of product which contains darkly colored by-products. Frequently such by-product containing products also have very strong and undesirable odors. For example, where weak catalysts are employed, more vigorous reaction conditions are often required, resulting in the formation of disulfide which is severely discolored due to decomposition of both starting material and product under the vigorous reaction conditions. Where strong catalysts are employed, reaction conditions must be closely controlled lest product decomposition become a major problem. In addition, many metal catalysts introduce impurities into the product which are difficult if not impossible to remove. As a result, product may retain traces of catalytic materials which may promote product degradation. Where amines are used as catalysts for the conversion of mercaptans to disulfides, even small amounts of catalytic material remaining in the product imparts objectionable odor to the product.

OBJECTS OF THE INVENTION

It is, therefore, an object of the present invention to provide a method for the oxidation of mercaptoalkanols to produce dithiodiglycol products having low odor and good color properties.

This and other objects of the invention will become apparent from inspection of the detailed description and claims provided herewith.

STATEMENT OF THE INVENTION

In accordance with the present invention, we have discovered that the oxidative conversion of mercaptoalkanols to produce dithiodiglycols is efficiently promoted by using very low levels of ammonia as catalyst. The resulting dithiodiglycol products are essentially odor free and retain very good color properties.

DETAILED DESCRIPTION OF THE INVENTION

In accordance with the present invention, there is provided a method for the conversion of mercaptoalkanols to dithiodiglycols which method comprises contacting the mercaptoalkanol with an oxygen-containing gas and anhydrous ammonia, wherein the mole ratio of ammonia to mercaptoalkanol is maintained below about 0.01:1.

The mercaptoalkanols contemplated to be useful in the practice of the present invention have the structure:

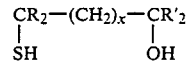

wherein each R and R' is independently either H or a $C_1$ up to $C_3$ alkyl radical and x is a whole number in the range of about 0 up to 3. Exemplary mercaptoalkanols which satisfy the above formula include 2-mercaptoethanol, 2-mercaptopropanol, 3-mercaptopropanol, 4-mercapto-2-butanol, 4-mercapto-1-butanol, and the like.

The product dithiodiglycols obtained in the practice of the present invention are represented by the following general formula:

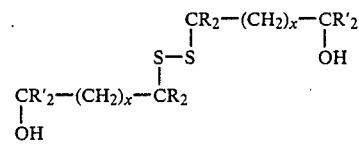

Thus, products such as di(2-hydroxyethyl)disulfide, di(3-hydroxypropyl)disulfide, di(4-hydroxybutyl)disulfide, and the like, are readily prepared by employing the invention method.

A wide range of reaction parameters are suitable for the practice of the present invention, as can readily be determined by one of skill in the art. In order to provide additional guidance, the following general values are suggested. Temperatures in the range of about 100 up to 200° F. are typically employed, with temperatures in the range of about 140° up to 170° F. preferred. While pressures employed for the invention reaction are not critical, pressures in the range of about 100 up to 500 psig are suitable, with pressures in the range of about 250 up to 400 psig preferred. The length of time over which the contacting of mercaptoalkanol with oxygen in the presence of anhydrous ammonia is carried out can vary within wide ranges. Typically, reaction is carried out for in the range of about 1 up to 24 hours, preferably in the range of about 2 up to 6 hours.

Suitable sources of oxygen-containing gas employed in the practice of the present invention include air, oxygen-enriched air, substantially pure oxygen streams, and the like. Presently preferred is substantially purified oxygen for best mercaptoalkanol conversions.

In order to produce product with essentially no residual amine odor and good color qualities, the ammonia/mercaptoalkanol molar ratio is maintained below about 0.01:1. Preferably for the best combination of product yield, product aroma and color properties, ammonia/mercaptoalkanol ratios will be maintained in the range of about 0.001:1 up to 0.006:1.

A particular advantage of the present invention is the fact that no added catalysts are needed for the oxidative coupling of mercaptoalkanols to produce dithiodiglycols. Thus, only the required low levels of ammonia are employed as catalyst and no metal-containing catalysts are employed for mercaptoalkanol conversion. Therefore, the resulting dithiodiglycol product is obtained substantially free of contamination from metal-containing catalysts. In addition, because the low odor, low color dithiodiglycol product obtained in the practice of the present invention is produced in essentially quantitative yield, the product can be used directly as obtained from the reaction vessel, with no need for product workup or purification.

A further understanding of the present invention and its advantages will be provided by reference to the following nonlimiting examples.

EXAMPLE I

2-Mercaptoethanol was oxidized with gaseous oxygen at a temperature in the range of about 150°–170° F. in the presence of small amounts of anhydrous ammonia. The 2-mercaptoethanol was charged to the reactor which was pressured to about 240 psig with nitrogen. Oxygen was then added to the system as required to maintain the desired reaction pressure (shown in Table I for each run). The mole ratio of ammonia/mercaptoalkanol charged to the reactor, reaction parameters and reaction results are summarized in Table I.

TABLE I

| | | Reaction Parameters | | | Reaction Results | | |
|---|---|---|---|---|---|---|---|
| Run | NH$_3$/BME* mole ratio | Temperature, °F. | Pressure, psig | Time, hr. | BME Conversion | Product Color | Product Odor |
| 1 (Control) | 0 | — | — | — | no reaction | — | — |
| 2 (Control) | 0.060:1 | 165 | 330 | — | 100 | Dark | Strong NH$_3$ odor |
| 3 (Control) | 0.030:1 | 165 | 330 | — | 100 | Dark | Strong NH$_3$ odor |
| 4 (invention) | 0.0057:1 | 140–170 | 310–340 | 2.0 | 100 | Light | Little odor |
| 5 (invention) | 0.0057:1 | 165 | 294–344 | 4.75 | 100 | Light | Little odor |
| 6 (invention) | 0.0029:1 | 150–170 | 265–330 | 2.75 | <100 | Light | Slight odor |
| 7 (invention) | 0.0057 | 145–165 | 259–290 | 5.0 | 100 | Light | Slight odor |

*BME = β-mercaptoethanol (2-mercaptoethanol)

Note that when the ammonia/mercaptoalkanol ratio is maintained below about 0.01:1, the product obtained has only a light color and very little odor, whereas control runs where greater than 0.01:1 ammonia/mercaptoalkanol ratio was employed gave dark product having a strong residual ammonia odor. Essentially quantitative conversion with high product yields are obtained in all invention runs, except where the ammonia/mercaptoalkanol ratio falls below about 0.003:1.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

That which is claimed:

1. A method for the conversion of a mercaptoalkanol having the structure:

$$\begin{array}{c} CR_2-(CH_2)_x-CR'_2 \\ | \qquad\qquad\qquad | \\ SH \qquad\qquad\quad OH \end{array}$$

wherein each R and R' is independently either H or a C$_1$ to C$_3$ alkyl radical and x is a whole number ranging between 0 and 3, to a dithiodiglycol having the structure:

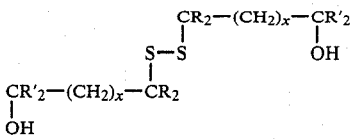

which comprises contacting said mercaptoalkanol with an oxygen-containing gas and anhydrous ammonia, wherein the mole ratio of ammonia to said mercaptoalkanol is maintained below about 0.01:1.

2. A method in accordance with claim 1 wherein said mercaptoalkanol is 2-mercaptoethanol.

3. A method in accordance with claim 1 wherein the ratio of ammonia to said mercaptoalkanol is maintained in the range of about 0.001:1 up to 0.006:1.

4. A method in accordance with claim 1 wherein said conversion is carried out at a temperature in the range of about 100° up to 200° F.

5. A method in accordance with claim 1 wherein said conversion is carried out at a pressure in the range of about 250 up to 400 psig.

6. A method in accordance with claim 1 wherein the contact time for said conversion is in the range of about 1 up to about 24 hours.

7. A method in accordance with claim 1 wherein said oxygencontaining gas is substantially pure oxygen.

* * * * *